United States Patent [19]

Ashmead et al.

[11] Patent Number: 5,596,016
[45] Date of Patent: Jan. 21, 1997

[54] 1,2-DISUBSTITUTED AROMATIC CHELATES

[75] Inventors: Stephen Ashmead, Clinton; Harvey H. Ashmead, Kaysville, both of Utah

[73] Assignee: Albion International, Inc., Clearfield, Utah

[21] Appl. No.: 293,516

[22] Filed: Aug. 19, 1994

[51] Int. Cl.$^6$ .......................... A61K 31/28; C07F 15/00; C07F 3/00; C07F 11/00

[52] U.S. Cl. .......................... 514/492; 514/494; 514/499; 514/501; 514/502; 556/1; 556/45; 556/50; 556/57; 556/62; 556/63; 556/113; 556/117; 556/135; 556/150

[58] Field of Search .................................. 556/45, 50, 57, 556/62, 63, 113, 117, 135, 150, 1; 514/492, 494, 501, 502, 499

[56] References Cited

PUBLICATIONS

Bullock et al., Inorganica Chimica Acta, vol. 19, No. 1, pp. 79–85 (1976).
Bullock et al., J. Chem. Soc. (A), pp. 2351–2355 (1971).
Bullock et al., J. Chem. Soc. (A), pp. 2472–2475 (1970).
Betran Martinez et al., Chemical Abstracts, vol. 75, No. 26, Chem. Abs. No. 157706f, p. 424 (1971).
Sellmann et al., J. Organomet. Chem., vol. 297, pp. 319–329 (1985).
James H. Weber, Syn. React. Inorg. Metal–Org. Chem., vol. 7, No. 3, pp. 243–252 (1977).
Anzai et al., Chemical Abstracts, vol. 88, No. 6, Abs. No. 41632t p. 248 (1978).
Anzai et al., Chemical Abstracts, vol. 88, No. 14, Abs. No. 94776z, p. 331 (1978).
Baslas, Chemical Abstracts, vol. 110, No. 2, Abs. No. 13371m, p. 328 (1989).

*Primary Examiner*—Porfirio Nazario-Gonzales
*Attorney, Agent, or Firm*—Thorpe, North & Western, L.L.P.

[57] ABSTRACT

Mineral absorption is promoted in warm-blooded animals by means of a class of 1,2-disubstituted aromatic mineral chelates wherein the 1 and 2 substituents each donates a pair of electrons to a metal ion for formation of a five-member chelate ring. 2-Alkoxyphenols are particularly preferred. The chelates contain from one to three alkoxyphenol ligands, with two ligands being preferred. A preferred alkoxyphenol is vanillin, and the minerals are selected from the group consisting of Mg, Ca, Cr, Mn, Fe, Co, Cu, Zn, Mo, and Se. Vanillin metal chelates have a slight to neutral taste, and are absorbed more readily than inorganic mineral salts.

28 Claims, 2 Drawing Sheets

1,2-DISUBSTITUTED AROMATIC CHELATES

BACKGROUND OF THE INVENTION

This invention relates to a chelated mineral composition containing 1,2-disubstituted aromatic ligands. More particularly, this invention relates to mineral chelates containing 1,2-disubstituted aromatic ligands and particularly 2-alkoxyphenol ligands, such as vanillin, and metals selected from the group consisting of Mg, Ca, Cr, Mn, Fe, Co, Cu, Zn, Se, and Mo wherein the ligand to metal ratio is 1:1 to 3:1, preferably 2:1.

When a metal combines with an electron donor, a complex or coordination compound is formed. When the electron donor, also referred to as a ligand or chelating agent, contains two or more donor groups tied together in some way, the resulting complex is a chelate. The essential and characteristic feature found in all chelates is formation of a ring between the ligand and the metal atom. For ring formation to occur, the electron donor molecule must contain two or more groups that can each combine with the metal atom with formation of at least one coordinate covalent bond. Also, groups or atoms (such as oxygen, nitrogen, hydroxyl, and amino) must be present that can coordinate with the metal atom through their lone electron pair. Further, these donor groups must be separated from each other by chains of suitable length to permit formation of rings with five or six member rings being most stable. Albert E. Frost, Fundamental Aspects of Chelation, The Science Counselor (June, 1956).

Amino acids comprise a group of ligands that have been used to chelate minerals. It is known that amino acid chelates form a stable product having one or more five-member rings formed by reaction between the carboxyl oxygen and the α-amino group of an a-amino acid with the metal ion. Such a five-member ring is defined by the metal atom, the carboxyl oxygen, the carbonyl carbon, the a-carbon, and the α-amino nitrogen and is generally represented by Formula I. However, the actual structure will depend upon the ligand to metal mole ratio. The ligand to metal mole ratio is at least 1:1 and is preferably 2:1, but in certain instances may be 3:1 or even 4:1 or higher. Most typically, an amino acid chelate may be represented at a ligand to metal ratio of 2:1 according to Formula I:

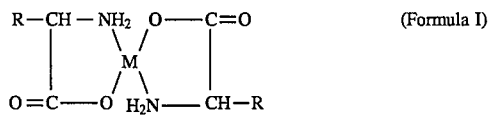
(Formula I)

In the above formula, when R is H, the amino acid is glycine, the simplest of the α-amino acids. However, R could represent any of the side chains of the other twenty or so naturally occurring amino acids derived from proteins. These α-amino acids all have the same configuration for the positioning of the carboxyl oxygen and the α-amino nitrogen. In other words, the chelate ring is defined by the same atoms in each instance. The American Association of Feed Control Officials (AAFCO) have also issued a definition for an amino acid chelate. It is officially defined as the product resulting from the reaction of a metal ion from a soluble metal salt with amino acids with a mole ratio of one mole of metal to one to three (preferably two) moles of amino acids to form coordinate covalent bonds. The average weight of the hydrolyzed amino acids must be approximately 150 and the resulting molecular weight of the chelate must not exceed 800. The products are identified by the specific metal forming the chelate, i.e. iron amino acid chelate, copper amino acid chelate, etc.

Amino acid chelates can also be formed using peptide ligands instead of single amino acids. These will usually be in the form of dipeptides or tripeptides because larger ligands would have a molecular weight which would be too great for direct assimilation of the chelate formed. Generally, peptide ligands will be derived by the hydrolysis of protein. However, peptides prepared by conventional synthetic techniques or genetic engineering can also be used. When a ligand is a di- or tripeptide, a radical of the formula [C(O)CHRNH]$_e$H will replace one of the hydrogens attached to the nitrogen atom in Formula I. R, as defined in Formula I, can be H, or the side chain of any other naturally occurring amino acid and e can be an integer of 1 or 2. When e is 1 the ligand will be a dipeptide and when e is 2 the ligand will be a tripeptide.

The structure, chemistry, and bioavailability of amino acid chelates is well documented in the literature, e.g. Ashmead et al., Chelated Mineral Nutrition, (1982), Chas. Co Thomas Publishers, Springfield, Ill.; Ashmead et al., Intestinal Absorption of Metal Ions, (1985), Chas. C. Thomas Publishers, Springfield, Ill.; Ashmead et al., Foliar Feeding of Plants with Amino Acid Chelates, (1986), Noyes Publications, Park Ridge, N.J.; as well as in U.S. Pat. Nos. 4,020,158; 4,167,564; 4,216,143; 4,216,144; 4,599,152; 4,774,089; 4,830,716; 4,863,898 and others. Flavored effervescent mixtures of vitamins and amino acid chelates for administration to humans in the form of a beverage are disclosed in U.S. Pat. No. 4,725,427.

In the field of mineral nutrition, amino acid chelates have increasingly been recognized as providing certain advantages over inorganic mineral salts. One advantage is attributed to the fact that these chelates are readily absorbed in the gut and mucosal cells by means of active transport as though they were small peptides. In other words, the minerals are absorbed along with the amino acids as a single unit utilizing the amino acids as carrier molecules. Since this method of absorption does not involve the absorption sites for free metal ions, the problems of competition of ions for active sites and suppression of one nutritive mineral element by another are avoided. Other advantages of amino acid chelates include stimulation of gonadotropic hormones, U.S. Pat. No. 4,774,089; delivery of metal ions to targeted tissue sites, U.S. Pat. No. 4,863,898; and enhancement of the immune system, U.S. Pat. No. 5,162,369.

Despite these advantages, use of amino acid chelates for human consumption has the drawback of a metallic aftertaste that some people find disagreeable. Thus, amino acid chelates have had to be taken in capsules and other forms that avoid the aftertaste. Use of amino acid chelates in nutritional beverages has also been limited by this aftertaste.

In view of the foregoing, it will be appreciated that mineral chelates that do not contain amino acids or an unpleasant aftertaste, yet provide the advantage of increased absorption of minerals compared to inorganic minerals, would be a significant advancement in the art.

OBJECTS AND SUMMARY OF THE INVENTION

It is an object of the present invention to provide mineral chelates wherein the mineral is in a bioavailable form but without the associated unpleasant taste attributed to the use of amino acids.

It is another object of the invention to provide mineral chelates that have a pleasant or neutral taste.

It is also an object of the invention to provide mineral chelates wherein the ligand is generally recognized by regulatory agencies as an acceptable food additive or supplement.

It is a further object of the invention to provide mineral chelates that are relatively non-polar so that they easily cross cellular membranes.

An additional object of the invention is to provide mineral chelates of 1,2-disubstituted aromatic molecules wherein the chelation positively affects the bioavailability and/or absorption of the bioactive molecule.

These and other objects are achieved by means of a chelate formed by reacting a 1,2-disubstituted aromatic moiety wherein the 1, 2 substituents are capable of reacting with a metal ion through coordinate covalent and/or coordinate bonding to form a five member chelate ring defined by the 1, 2 carbon atoms of the aromatic ring, the 1 and 2 substituents and the metal ion. The 1,2-disubstituted aromatic moiety is represented by Formula II:

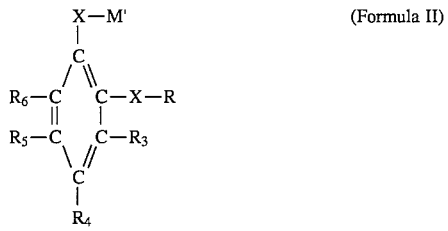

(Formula II)

where X is an electron donor member selected from the group consisting of O, S, or NH; M' is member selected from the group consisting of H, Na, K, or $NH_4$ with the proviso that when X is NH, M' is H; R is a member selected from the group consisting of alkyl and alkenyl containing from 1 to 10 carbon atoms, preferably 1 to 5 carbon atoms; $R_3$ and $R_6$ are independently members selected from the group consisting of H and R; and $R_4$ and $R_5$ are independently members selected from the group consisting of H, R, R', $NH_2$, NHR, NHR', OH, SH, COOR, COOR', and CHO. R' is an R group which had been additionally substituted by one or more members selected from the group consisting of COOH, $NH_2$, NHR, OH, SH, and COOR. The metal ion ("M") utilized in the chelate formation is selected from the group consisting of Mg, Ca, Cr, Mn, Fe, Co, Cu, Zn, Se, and Mo and is present in a form suitable for reaction. M is preferably present as a soluble metal salt, such as a chloride, sulfate, nitrate, or acetate.

DETAILED DESCRIPTION OF THE INVENTION

Figure 1:
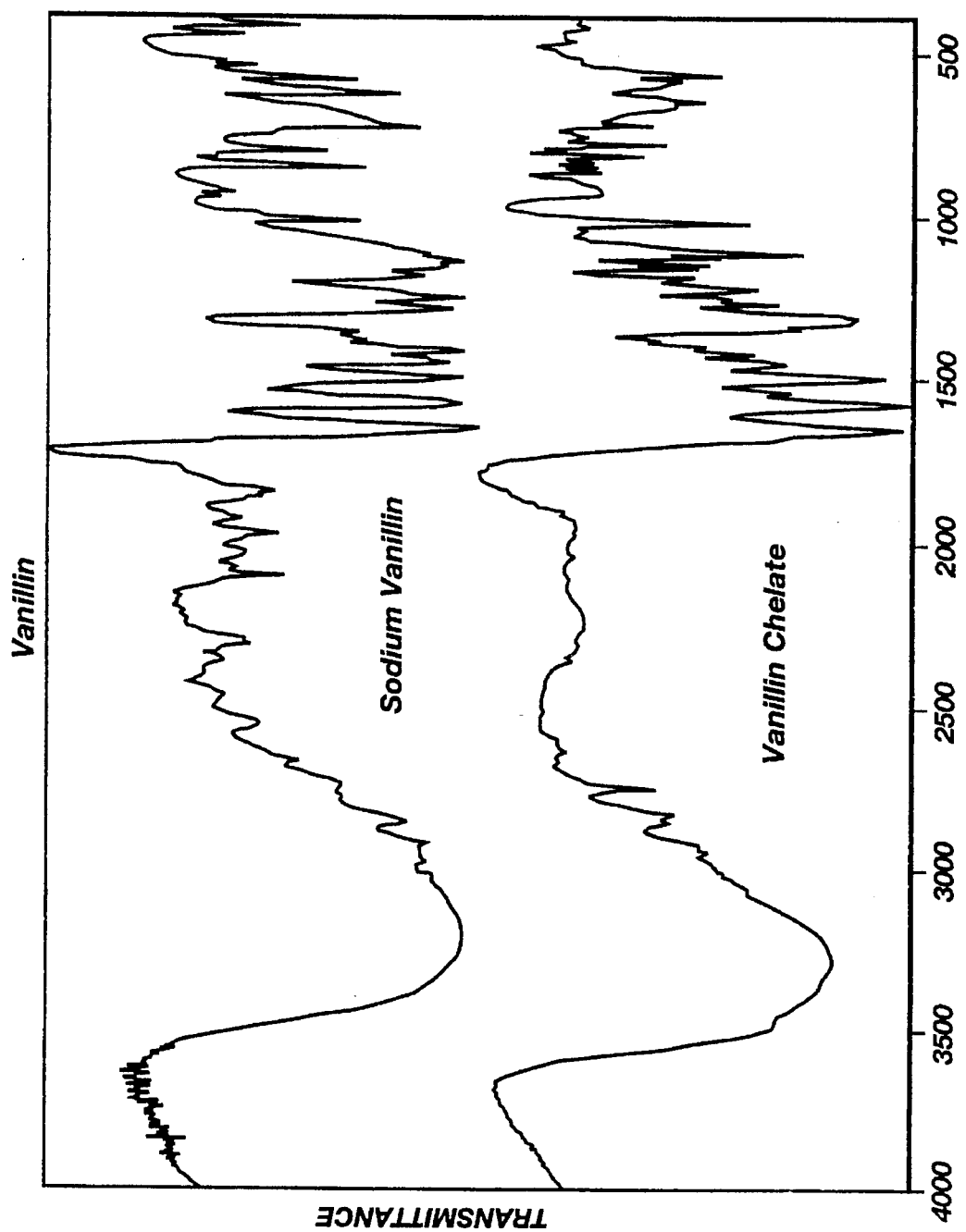
FIG. 1 is an FT-IR spectrum comparing vanillin and $Na^+$vanillin$^-$.

Before the present 1,2-disubstituted aromatic mineral chelate compositions and methods of making them are disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims and their equivalents.

There are many 1,2-disubstituted aromatic compounds found in nature which possess the formula:

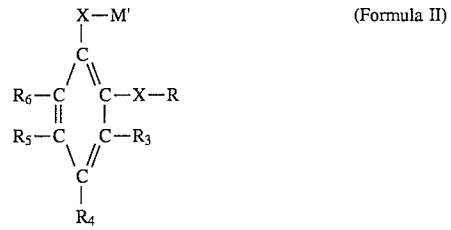

(Formula II)

where X is an electron donor member selected from the group consisting of O, S, or NH; M' is member selected from the group consisting of H, Na, K, or $NH_4$ with the proviso that when X is NH, M' is H; R is a member selected from the group consisting of alkyl and alkenyl containing from 1 to 10 carbon atoms, preferably 1 to 5 carbon atoms; $R_3$ and $R_6$ are independently members selected from the group consisting of H and R; and $R_4$ and $R_5$ are independently members selected from the group consisting of H, R, R', $NH_2$, NHR, NHR', OH, SH, COOR, COOR', and CHO. R' is an R group which had been additionally substituted by one or more members selected from the group consisting of COOH, $NH_2$, NHR, OH, SH, and COOR. There is a proviso that none of the $R_3$ through $R_6$ substituents can be more polar than the 1,2 ring substituents so as to tend to withdraw electrons from these substituents which would inhibit or prevent their chelate forming characteristics.

Prominent among the 1,2-disubstituted aromatic compounds, and preferred in the present invention are the 2-alkoxyphenols, i.e. where X is O. Particularly preferred are vanillin and guaiacol. For vanillin X is O, M' is H, R is $CH_3$, $R_3$, $R_5$, and $R_6$ are H, and $R_4$ is —CHO. For guaiacol (o-methoxyphenol; methylcatechol; o-hydroxyanisole; 1-hydroxy-2-methoxybenzene) X is O, M' is H, R is $CH_3$, and $R_3$, $R_4$, $R_5$, and $R_6$ are H. To be technically correct, vanillin is a benzaldehyde derivative and the numbering of the carbon atoms on the aromatic ring begins with the aldehyde carbon and thus has the name 4-hydroxy-3methoxybenzaldehyde. However, for purposes of the present invention, the numbering on the aromatic ring begins with the carbon containing the XM' group as the 1 carbon and the adjacent carbon containing the XR group is the 2 carbon. Therefore the subscript on substituents $R_3$ through $R_6$ is representative of the carbon atom position on the aromatic ring to which they are attached.

Although not specifically numbered in accordance with the above described terminology, representative of other compounds meeting the 1,2-disubstituted aromatic ligand criteria are o-anisidine (2-methoxybenzenamine), 2,4-diaminoanisole (4-methoxy-m-phenylenediamine), 2-methylaminophenol, o-thioanisidine, 2-methylaminothiophenol, 4-hydroxy-3-methoxytoluene, 4-hydroxy-3-methoxy-α-(aminomethyl)benzyl alcohol (Normetanephrine), 4-hydroxy-3-methoxybenzenacetic acid (homovanillic acid), 4-hydroxy-3-methoxycinnamic alcohol (coniferyl alcohol), 3-methoxy-4-hydroxytoluene (creosol; 2-methoxy-4-methylphenol), L-3-methoxy-4-hydroxyphenylalanine (3-O-methyldopa), and the like.

2-Alkoxyphenols, such as vanillin, and guaiacol are found in a wide variety of forms in almost all foods. These compounds have the necessary atoms and groups to function as electron donors for formation of covalent bonds with metals that are needed to form stable chelates. Further, 2-alkoxyphenols contain resonance electrons in the benzene ring that can contribute to the stabilization of mineral chelates containing such ligands. Due to their relatively non-polar structure, particularly when $R_4$ and $R_5$ are H or unsubstituted R groups, there may be enhanced transport across cellular membranes. As noted above, the thio and amine analogs of the phenol or the alkoxy group, which can contribute or donate electrons in the formation of chelates, can be used in the place of the phenol or alkoxy groups. By alkoxy is meant so-called lower alkyl groups usually containing from one to ten carbon atoms and preferably from one to five carbon atoms. Methoxy is the preferred alkoxy group.

The invention will be primarily described in terms of 2-alkoxyphenols as the ligand source. However, by analogy, any of the 1,2-disubstituted aromatic ligands could also be utilized.

2-Alkoxyphenols are capable of being ligands for forming metal chelates because the alkoxy oxygen atom and the hydroxyl oxygen atom are suitably located to donate electrons to a metal ion for formation of coordinate covalent bonds required for formation of a chelate ring structure. Mineral 2-alkoxyphenol chelates are synthesized by reacting a 2-alkoxyphenol with a hydroxide of a monovalent cation, such as an alkali metal hydroxide or ammonium hydroxide, to form a monovalent cation salt of the 2-alkoxyphenol. In this reaction, the hydroxide of a monovalent cation removes a hydrogen ion from the 1-hydroxyl group of the 2-alkoxyphenol to form the monovalent cation salt at this position. This reaction renders the 2-alkoxyphenol molecule readily soluble in aqueous solution and also ionizes the 2-alkoxyphenol for forming a chelate. A soluble metal salt, such as a chloride, sulfate, nitrate or acetate, wherein the metal is selected from the group consisting of Mg, Ca, Cr, Mn, Fe, Co, Cu, Zn, Mo, and Se is then added to the aqueous solution containing the alkoxyphenol salt. The metal and the monovalent cation exchange places, and the 1-hydroxyl oxygen of the alkoxyphenol donates two electrons to form a covalent bond between this oxygen atom and the metal. Further, the oxygen atom of the 2-alkoxy group also donates two electrons to form a second covalent bond with the metal. The resulting chelate contains a five-member ring defined by the metal atom, the 2-alkoxy oxygen, the 2-carbon, the 1-carbon, and the 1-hydroxyl oxygen. The ligand to metal mole ratio is at least 1:1 and is preferably 2:1, but in certain instances may be 3:1 or even higher. This reaction scheme is expressed for a ligand to metal mole ratio of 2:1 according the following formula:

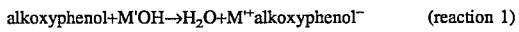

alkoxyphenol+M'OH→H$_2$O+M'$^+$alkoxyphenol$^-$   (reaction 1)

2M'$^+$alkoxyphenol$^-$+M·B$_n$→M(alkoxyphenol)$_2$+n M'$_m$B (reaction 2)

wherein M' is a monovalent cation; B is an anion of a soluble salt such as the Cl$^-$, NO$_3^-$, CH$_3$COO$^-$, or SO$_4^{2-}$ anion; M is a metal selected from the group consisting of Mg, Ca, Mn, Fe(II), Co, Cu(II), Zn, Mo, and Se; n is 1 or 2; and m is 1 or 2, with the proviso that when B is a divalent anion, i.e., the SO$_4^{2-}$ anion, then n is 1 and m is 2, and when B is a monovalent anion, i.e., a Cl$^-$, NO$_3^-$ or CH$_3$COO$^-$ anion, then n is 2 and m is 1. The reaction of the monovalent cation salt of the 2-alkoxyphenol with the metal salt is expressed for a ligand to metal mole ratio of 3:1 according to the following formula:

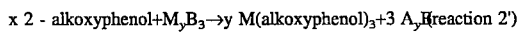

x 2 - alkoxyphenol+M$_y$B$_3$→y M(alkoxyphenol)$_3$+3 A$_y$B (reaction 2')

wherein x is an integer of 3 or 6; M is Fe(III) or Cr; B is as described above; and y is an integer of 1 or 2 with the proviso that when B is a monovalent anion then x is 3 and y is 1, and when B is a divalent anion then x is 6 and y is 2.

A 1,2-disubstituted aromatic mineral chelate according to the present invention may be represented by Formula III:

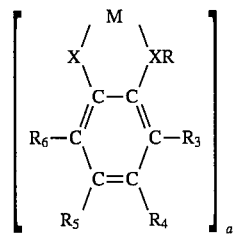

(Formula III)

wherein a is an integer of 1, 2, or 3; M is a metal ion selected from the group consisting of Mg, Ca, Cr, Mn, Fe, Co, Cu, Zn, Mo, and Se; X is an electron donor member selected from the group consisting of O, S, or NH; R is a member selected from the group consisting of alkyl and alkenyl containing from 1 to 10 carbon atoms; $R_3$ and $R_6$ are members independently selected from the group consisting of H and R; $R_4$ and $R_5$ are independently members selected from the group consisting of H, R, R', NH$_2$, NHR, NHR', OH, SH, COOR, COOR', and CHO; and R' is an R group which had been additionally substituted by one or more members selected from the group consisting of COOH, NH$_2$, NHR, OH, SH, and COOR.

A 2-alkoxyphenol mineral chelate may be represented according to Formula IV:

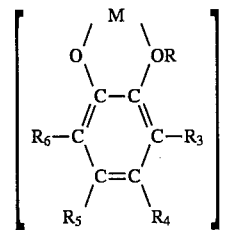

(Formula IV)

wherein a is an integer of 1, 2, or 3; M is a metal ion selected from the group consisting of Mg, Ca, Cr, Mn, Fe, Co, Cu, Zn, Mo, and Se; and R, $R_3$–$R_6$ are as defined above.

As previously noted, a preferred alkoxyphenol is vanillin (3-methoxy-4-hydroxyl-benzaldehyde). Vanillin is a known and accepted food ingredient that is generally regarded as safe. It has both a pleasing odor and taste, and is relatively easy to obtain in pure form.

Mineral vanillin chelates can be synthesized by reacting vanillin with a hydroxide of a monovalent cation, such as an alkali metal hydroxide or ammonium hydroxide, to form a vanillin salt, and then adding a soluble metal salt such as a chloride, sulfate, nitrate or acetate to result in formation of the vanillin chelate. An example of such reactions is expressed according to the following schemes, using NaOH as a preferred alkali metal hydroxide and a metal chloride to prepare a vanillin metal chelate with a ligand to metal mole ratio of 2:1:

vanillin+NaOH→H$_2$O+Na$^+$vanillin$^-$   (reaction 3)

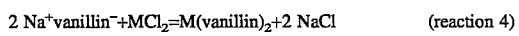

2 Na$^+$vanillin$^-$+MCl$_2$=M(vanillin)$_2$+2 NaCl   (reaction 4)

A vanillin chelate may be represented at a ligand to metal ratio of 2:1 according to the following formula:

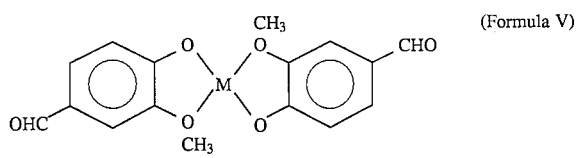

(Formula V)

The five-member chelate ring may be further stabilized by the π-electrons of the benzene ring. The vanillin chelate is less polar than vanillin per se, and precipitates out of solution at concentrations where vanillin is soluble. In addition to solubility in aqueous solution, vanillin chelates have other properties that differ from the parent compounds, such as taste, melting point, infrared spectroscopy, and elemental analysis, further indicating the formation of metal chelates. The aldehyde functional group of the vanillin molecule is not believed to be involved in the reaction.

The following examples are illustrative of numerous 2-alkoxyphenol chelates falling within the scope of the invention and means of their preparation. The data presented show the best mode presently known of practicing the invention using vanillin and guaiacol as ligands through which the covalent bonds are formed with the metal.

EXAMPLE 1

To a solution of 0.40 g (0.01 mole) of NaOH in 10 ml of distilled water (1M NaOH) was added 1.52 g (0.01 mol) of vanillin. Warming of the mixture of ingredients to about 42° C. speeded the rate of the reaction. The vanillin dissolved in the NaOH solution, resulting in formation of the sodium salt of vanillin (Na-vanillin) by removal of the 4-hydroxyl hydrogen from vanillin and formation of an ionic bond between the $Na^+$ ion in solution and the $O^-$ remaining at the 4 position, according to reaction 3 described above.

EXAMPLE 2

To a solution containing 0.80 g (0.02 mole) of NaOH in 20 ml of distilled water (1M NaOH) was added 3.04 g (0.02 mole) of vanillin. The mixture was warmed to about 42° C. until the vanillin went into solution, then 2.00 g (0.01 mole) of $MgCl_2 \cdot 2H_2O$ was added while stirring. A yellowish white precipitate was formed. This precipitate is a chelate according to reaction 4, containing a ligand to metal ratio of 2:1. The precipitate was collected by vacuum filtration, washed with 20 ml of distilled water, and dried.

EXAMPLE 3

The sodium salt of vanillin was prepared according to Example 2, and then 1.47 g (0.01 mole) of $CaCl_2 \cdot 2H_2O$ was added while stirring. A white precipitate, which is a chelate according to reaction 4, was formed containing a ligand to metal ratio of 2:1. The precipitate was collected by vacuum filtration, washed with 20 ml of distilled water, and dried.

EXAMPLE 4

The sodium salt of vanillin was prepared according to Example 2, and then 1.55 g (0.01 mole) of $CoCl_2 \cdot 6H_2O$ was added while stirring. A greenish precipitate, which is a chelate according to reaction 4, was formed containing a ligand to metal ratio of 2:1. The precipitate was collected by vacuum filtration, washed with 20 ml of distilled water, and dried.

EXAMPLE 5

The sodium salt of vanillin was prepared according to Example 2, and then 1.99 g (0.01 mole) of $Fe(II)Cl_2 \cdot 4H_2O$ was added while stirring. A brownish precipitate was formed, which then turned yellow-green. This precipitate is a chelate according to reaction 4, containing a ligand to metal ratio of 2:1. The precipitate was collected by vacuum filtration, washed with 20 ml of distilled water, and dried.

EXAMPLE 6

The sodium salt of vanillin was prepared according to Example 2, and then 1.71 g (0.01 mole) of $Cu(II)Cl_2 \cdot 2H_2O$ was added while stirring. A reddish-brown precipitate, which is a chelate according to reaction 4, was formed, containing a ligand to metal ratio of 2:1. The precipitate was collected by vacuum filtration, washed with 20 ml of distilled water, and dried.

EXAMPLE 7

The sodium salt of vanillin was prepared according to Example 2, and then 1.36 g (0.01 mole) of $ZnCl_2$ was added while stirring. A bright white precipitate, which is a chelate according to reaction 4, was formed, containing a ligand to metal ratio of 2:1. The precipitate was collected by vacuum filtration, washed with 20 ml of distilled water, and dried.

EXAMPLE 8

The sodium salt of vanillin was prepared according to Example 2, and then 1.98 g (0.01 mole) of $MnCl_2 \cdot 4H_2O$ was added while stirring. A bright yellow precipitate, which is a chelate according to reaction 4, was formed, containing a ligand to metal ratio of 2:1. The precipitate was collected by vacuum filtration, washed with 20 ml of distilled water, and dried.

EXAMPLE 9

To a solution containing 1.20 g (0.03 mole) of NaOH in 30 ml of distilled water (1M NaOH) was added 4.56 g (0.03 mole) of vanillin. The mixture was warmed to about 42° C. until the vanillin went into solution, then 2.66 g (0.01 mole) of $CrCl_3 \cdot 6H_2O$ was added while stirring. A gray-green precipitate, which is a chelate according to reaction 2', was formed containing a ligand to metal ratio of 3:1. The precipitate was collected by vacuum filtration, washed with 20 ml of distilled water, and dried.

EXAMPLE 10

To a solution containing 2.24 g (0.04 mole) of KOH in 40 ml of distilled water (1M KOH) was added 6.08 g (0.04 mole) of vanillin. The mixture was warmed to about 42° C. until the vanillin went into solution, then 3.96 g (0.02 mole) of $MnCl_2 \cdot 4H_2O$ was added while stirring. A bright yellow precipitate, which is a chelate according to reaction 2, was formed, containing a ligand to metal ratio of 2:1. The precipitate was collected by vacuum filtration, washed with distilled water, and dried.

EXAMPLE 11

To a solution containing 4.84 g (0.04 mole) of $NH_4OH$ in 30 ml of distilled water (1.33M $NH_4OH$) was added 6.08 g (0.04 mole) of vanillin. The mixture was warmed to about 42° C. until the vanillin went into solution, then 3.98 g (0.02 mole) of $Fe(II)Cl_2 \cdot 4H_2O$ was added while stirring. A yellow-green precipitate, which is a chelate according to reaction 2, was formed, containing a ligand to metal ratio of 2:1. The precipitate was collected by vacuum filtration, washed with distilled water, and dried.

EXAMPLE 12

To test the mechanism of chelate formation described above, vanillic acid (4-hydroxy-3-methoxybenzoic acid) was substituted for vanillin in the reaction schemes described above for synthesis of vanillin chelates. To a solution containing 0.40 g (0.01 mole) of NaOH was added 1.68 g (0.01 mole) of vanillic acid. The vanillic acid slowly dissolved in the NaOH solution upon application of heat, resulting in a brown-colored solution. To the vanillic acid solution was added 0.99 g (0.005 mole) of $MnCl_2 \cdot 4H_2O$. The $MnCl_2$ went into solution without formation of a precipitate.

EXAMPLE 13

A vanillic acid solution was prepared according to Example 12. To this solution was added 0.68 g (0.005 mole) of $ZnCl_2$. The $ZnCl_2$ dissolved in the vanillic acid solution, resulting in a milky white and tan color, without formation of a precipitate.

EXAMPLE 14

A vanillic acid solution was prepared according to Example 12. To this solution was added 0.78 g (0.005 mole) of $CoCl_2 \cdot 6H_2O$. The $CoCl_2$ dissolved in the vanillic acid solution, resulting in a milky color, without formation of a precipitate.

Examples 12–14 show that vanillic acid did not react in the same way as previously described for vanillin. This was expected, because the $pK_a$ of the carboxyl group is lower than that of the phenol group. Hence, it was expected that the NaOH would pull a hydrogen ion from the carboxyl group instead of the hydroxyl group, forming an organic acid salt. When the metal chloride was added to the aqueous organic acid salt solution, it was expected that there would be a simple ion exchange of the metal ion for the $Na^+$ ion, thus forming another organic acid salt. The failure to form a precipitate when vanillic acid was substituted for vanillin is evidence that vanillic acid salts were formed instead of metal chelates. This evidence also suggests that the aldehyde group of vanillin is not involved in ionization in the presence of base. This evidence further suggests that chelate formation involves functional groups bonded to adjacent carbon atoms of the benzene ring, since the functional groups attached to the carbons at positions 1 and either 3 or 4 of vanillic acid are apparently too distant from each other to form a chelate.

EXAMPLE 15

To further test the mechanism of chelate formation described above, guaiacol (1-hydroxy-2-methoxybenzene) was substituted for vanillin in the reaction schemes described above for synthesis of vanillin chelates. To a solution containing 0.40 g (0.01 mole) of NaOH was added 1.24 g (0.01 mole) of guaiacol. To the guaiacol solution was added 0.99 g (0.005 mole) of $MnCl_2 \cdot 4H_2O$. A yellowish-tan precipitate was formed. This precipitate is a chelate according to reaction 2, containing a ligand to metal ratio of 2:1.

EXAMPLE 16

A guaiacol solution was prepared according to the procedure of Example 15. To the guaiacol solution was added 0.68 g (0.005 mole) of $ZnCl_2$. A white precipitate was formed. This precipitate is a chelate according to reaction 2, containing a ligand to metal ratio of 2:1.

EXAMPLE 17

A guaiacol solution was prepared according to the procedure of Example 15. To the guaiacol solution was added 0.78 g (0.005 mole) of $CoCl_2 \cdot 6H_2O$. A violet precipitate was formed. This precipitate is a chelate according to reaction 2, containing a ligand to metal ratio of 2:1.

Examples 15–17 show that the simplest 2-alkoxyphenol, guaiacol, functions as a ligand in chelation of minerals according to the reaction scheme of reactions 1 and 2.

EXAMPLE 18

A solution was prepared by dissolving 92.0 g (2.30 mole) of solid NaOH in 500 ml of distilled water. To this NaOH solution was added 350 g (2.30 mole) of vanillin. When the vanillin was dissolved, the solution was a clear yellow. Then, 321 g of $Fe(II)SO_4$ was added to the solution and permitted to react. A yellowish green precipitate was formed, although the precipitate was slower to form than with the chloride form of iron as would be expected due to the solubility differences between sulfates and chlorides. The precipitate was collected by filtration, then the precipitate was dried for three additional days at 65° C. The precipitate was a chelate according to the scheme of reactions 1 and 2.

EXAMPLE 19

A solution was prepared by dissolving 19.737 g (0.5 mole) of solid NaOH in 500 ml of distilled water. To this NaOH solution was added 75 g (0.5 mole) of vanillin. When the vanillin was dissolved, the solution was clear and yellow. Then, 60.42 g of $MgSO_4$ (0.25 mole) was added to the solution and permitted to react. A cream colored precipitate was formed, although the precipitate was slower to form than with the chloride form of magnesium. The precipitate was collected by filtration, then dried at 60° C. The precipitate was a chelate according to the scheme of reactions 1 and 2.

EXAMPLE 20

A Na-vanillin solution was prepared according to the procedure of Example 19. Then, 72.89 g (0.25 mole) of $ZnSO_4$ was added to the solution and permitted to react. A white precipitate was formed, although the precipitate was slower to form than with the chloride form of zinc. The precipitate was collected by filtration, then dried at 60° C. The precipitate was a chelate according to the scheme of reactions 1 and 2.

EXAMPLE 21

A Na-vanillin solution was prepared according to the procedure of Example 19. Then, 42.33 g (0.25 mole) of $MnSO_4$ was added to the solution and permitted to react. A yellow precipitate was formed, although the precipitate was slower to form than with the chloride form of manganese. The precipitate was collected by filtration, then dried at 60°

C. The precipitate was a chelate according to the scheme of reactions 1 and 2.

EXAMPLE 22

A Na-vanillin solution was prepared according to the procedure of Example 19. Then, 62.66 g (0.25 mole) of $CuSO_4$ was added to the solution and permitted to react. A precipitate was formed, although the precipitate was slower to form than with the chloride form of copper. The precipitate was collected by filtration, then dried at 60° C. The precipitate was a chelate according to the scheme of reactions 1 and 2.

EXAMPLE 23

A Na-vanillin solution was prepared according to the procedure of Example 19. Then, 38.24 g (0.25 mole) of $CoSO_4$ was added to the solution and permitted to react. A precipitate was formed, although the precipitate was slower to form than with the chloride form of cobalt. The precipitate was collected by filtration, then dried at 60° C. The precipitate was a chelate according to the scheme of reactions 1 and 2.

Fourier Transformed Infrared Spectroscopy (FT-IR)

FT-IR analysis was performed on 2-alkoxyphenol mineral chelates and vanillic acid compounds prepared as described above according to standard KBr pellet techniques with a sample inclusion rate of 2.5%.

Figure 2:
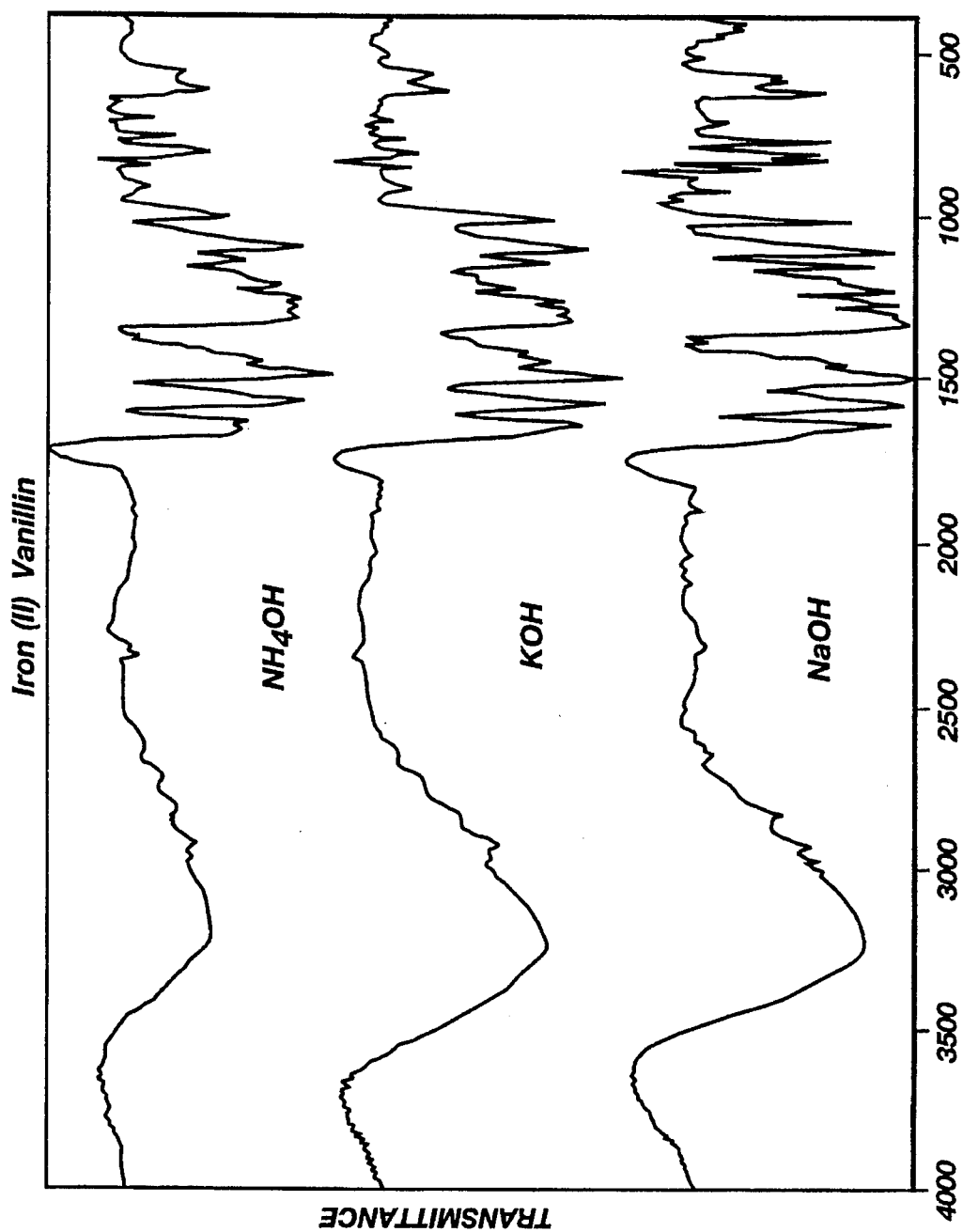
FIG. 2 is an FT-IR spectrum of a vanillin metal chelate prepared with NaOH (top), KOH (middle), and $NH_4OH$ (bottom).

FIG. 1 shows that in comparing vanillin to $Na^+vanillin^-$, there is a slight sharpening of the broad OH peak around $3000 \ cm^-$. This result is consistent with the structure of $Na^+vanillin^-$ previously described, wherein the Na cation exchanges with the hydrogen ion of the hydroxyl group. This sharpening of the OH peak is also apparent in all of the vanillin metal chelates as represented by FIG. 2, indicating that the metal ion is bonding with this hydroxyl oxygen and changing the spectral characteristics of the hydroxyl group on the vanillin molecule.

It is also evident from FIG. 1 that the aldehyde group of the vanillin molecule is not involved in bond formation with metal ions. According to Colthup et al., Introduction to Infrared and Raman Spectroscopy, Academic Press, Inc., San Diego, Calif., 1990, aldehyde CH vibrations give rise to two peaks at $2900–2800 \ cm^-$ and $2775–2695 \ cm^-$. However, when the aldehyde is attached to a benzene ring and is ortho to a halogen, nitro group, or methoxy group, as is the case in vanillin, these peaks shift to $2900–2860 \ cm^-$ and $2765–2747 \ cm^-$. These latter peaks are observed in the spectra obtained from analysis of vanillin and vanillin mineral chelates. If the aldehyde group was involved in bonding to the metal, changes in the peak wavenumber would be expected as they were evident with the OH peak. However, the peak wavenumbers are within the resolution tolerances for vanillin, $Na^+vanillin^-$, and the vanillin mineral chelates. It could be argued that bonding of a metal and vanillin could occur through the carbonyl oxygen of the aldehyde group and not with the CH portion of the aldehyde. If that were the case, then changes in the peaks associated with the carbonyl oxygen portions of benzaldehydes, at $1710–1685 \ cm^-$, would be expected. In fact, there is no change in the peaks associated with carbonyl oxygen among the vanillin, $Na^+vanillin^-$, and vanillin metal chelates. These data provide conclusive evidence that bonding between the vanillin molecule and the metal ion in the vanillin metal chelates does not involve the aldehyde group.

A methoxy group attached to a benzene ring gives rise to two bands in the ranges of $1310–1210 \ cm^-$ and $1050–1010 \ cm^-$, according to Colthup et al. Indeed, analysis of vanillin yields peaks centered at $1260 \ cm^-$ and $1030 \ cm^-$ that are attributable to the methoxy group. If the methoxy group is involved in bonding to the metal as was theorized, then these two peaks would be expected to shift in wave number. As shown in FIG. 2, these two peaks shift to $1023 \ cm^-$ and $1276 \ cm^-$, respectively, in the vanillin metal chelates. These results confirm the involvement of the methoxy group in bond formation with the metal ion.

Physical Properties of Vanillin Metal Chelates

The solubility of vanillin metal chelates is substantially lower than either vanillin or $Na^+vanillin^-$. When the vanillin metal chelates are formed they immediately precipitate from solution. Such solution is generally at a pH of between about 1 and 4. This result suggests that the solubility of these chelates in an aqueous environment at this pH range is slight. This property makes purification of chelates simple and could be advantageous for certain applications wherein minimal solubility in aqueous solution is desired. However, at a pH of higher than about 4 the vanillin metal chelates become soluble. Vanillin metal chelates also exhibit limited solubility in alcohol, which is, however, still less than that of vanillin. The solubility of vanillin chelates is opposite that of amino acid chelates which are soluble at a pKa lower than the zwitterion state and precipitate when the pKa is raised above the zwitterion state.

The melting points of vanillin metal chelates differ from that of vanillin. Vanillin has a melting point between 70° and 80° C. Vanillin metal chelates, however, were heated to temperatures over 100° C. with no evidence of melting.

The taste characteristics of vanillin metal chelates also are different than that of vanillin. Vanillin has a pleasing taste and odor. Vanillin metal chelates exhibit slight to neutral taste characteristics. There is no metallic aftertaste, as is common with amino acid chelates, and if the vanillin metal chelates are washed and filtered, there is no salty taste.

Atomic absorption spectroscopy and UV spectrophotometry also indicate that vanillin metal chelates have been formed. However, there are indications the metal is not 100% chelated. Table 1 shows that in 7 of 8 cases the observed weight percent metal in the chelates is more than the theoretical value. It may be that metal hydroxides form with excess hydroxide present in the reaction. It may be, also, that when chelation occurs, there is a proportion of chelates with a ligand to metal ratio lower than the expected ratio based on the ratio of vanillin salt and metal added to the reaction mixture. This may be due to non-simultaneous formation of chelate rings and precipitation of a chelate as soon as a first chelate ring is formed. Such precipitation may render the chelate unavailable for binding additional ligands. These findings suggest that optimization of the reaction conditions can be pursued, but do not detract from the fact that chelates are synthesized according the reactions presented herein.

TABLE 1

| Vanillin Metal | Percent Metal | |
| --- | --- | --- |
| Chelate | Observed | Theoretical* |
| Mg | 12.01 | 7.44 |
| Ca | 18.00 | 11.71 |

TABLE 1-continued

| Vanillin Metal Chelate | Percent Metal | |
|---|---|---|
| | Observed | Theoretical* |
| Co | 30.69 | 16.31 |
| Fe | 25.31 | 15.59 |
| Cu | 32.33 | 17.60 |
| Mn | 25.10 | 15.38 |
| Zn | 12.22 | 17.78 |
| Cr | 26.00 | 10.29 |

*The theoretical percent metal is based on a 2:1 mole ratio of ligand to metal, except for chromium vanillin chelate which is based on a 3:1 mole ratio.

Absorption of Vanillin Metal Chelates In Vivo

Toxicity: An iron (FeII) vanillin chelate was prepared according to Example 11 and adjusted to 15% by weight iron by the addition of agar. Similarly, a ferrous sulfate salt was adjusted to 15% by weight iron by the addition of agar. Rats were force fed No. 4 gelatin capsules containing each of these preparations to determine toxicity. Insufficient Fe-vanillin chelate could be administered to cause toxicity in any of the subjects.

Bioavailability: One gram samples of each of the above iron vanillin chelates and ferrous sulfate sales were administered orally to rats as a slurry consisting of one gram of sample contained in 4 ml of water. The samples were given via a syringe fitted with a balled needle and injected into the stomach of the animals. Each one gram sample of 15% iron would deliver 150 mg of Fe which is ten times the recommended daily allowance of iron for a human being of average size. Obviously, such a dosage is many times higher than required for the test animals considering that the rats weighed an average of about 125 grams each. One sample of two grams of chelate suspended as a slurry in 8 ml of water was found too be too much volume and overfilled the stomach of the rat resulting in the loss of some of the dosage.

The animals were observed over a two day (48 hour) period and their urine and feces were collected. At the end of the 48 hour period the animals were sacrificed and blood samples were taken.

The rats fed the iron vanillin chelate appeared normal, reactive to sound and consumed normal amounts of food and water. On the other hand, the rats fed the same dosage of iron as ferrous sulfate appeared listless and produced little urine and feces. They consumed no food or water for approximately 26 hours post dosage. One of the ferrous sulfate fed rats demonstrated hematuria within 2.5 hours following dosage. The ferrous sulfate fed rats were listless, non-reactive, retired and demonstrated abnormal breathing behavior.

There follows a comparison of the urine, feces and blood tests taken from the rats at 24 and 48 hours post dosage.

TABLE 2

| Time (hours) | Urine: (Total Mg Fe/ Total Gm Sample) | |
|---|---|---|
| | Fe Vanillate | FeSO$_4$ |
| 24 | 9.62/3.6 g | 1.18/1.5 g |
| 48 | 21.3/7.2 g | 61.6/2.6 g |

TABLE 3

| Time (hours) | Urine: (Total Mg Fe/ Total M1 Sample) | |
|---|---|---|
| | Fe Vanillate | FeSO$_4$ |
| 24 | 0.047/9.9 ml | 0.020/4.3 ml |
| 48 | 0.036/11.0 ml | 0.010/11.3 ml |

TABLE 4

| Time (hours) | Blood: (Mg Fe/M1 Blood) | |
|---|---|---|
| | Fe Vanillate | FeSO$_4$ |
| 24 | — | — |
| 48 | 0.53 | 0.30 |

As can be seen from a comparison of the results in Tables 2, 3 and 4, the rats fed the iron vanillate retained much more iron than those fed the ferrous sulfate salt. The iron vanillate is absorbed more rapidly as shown by higher levels in urine and feces after 24 hours. However, much more iron is retained within the animal as shown by the much higher excretion of iron in the feces from the iron sulfate group after 48 hours. Also, the iron in the blood was much higher in the iron vanillate group than in the ferrous sulfate group.

The exact amount of 1,2-disubstituted aromatic metal chelate to be administered may depend upon the particular need of the animal to which it is administered. It is not feasible to categorically state that a certain amount of mineral per kg of animal body weight is what is to be administered. For any animal species in which a recommended dietary allowance (RDA) or similar nutritional guideline has been established, that amount may be used as a guideline for determining the "effective" amount to be administered to that species per day. Generally, amounts ranging from about 25 to 500% of the established RDA, or other nutritional guideline, for the mineral being administered may be considered as an "effective amount." Furthermore, the ligand may also play an important role in determining just what an effective amount might be. For example, the L-3-methoxy-4-hydroxyphenylalanine (3-O-methyldopa) ligand contains both the alkoxy phenol and α-amino acid functions. This ligand is a major metabolite of L-dopa in both man and animals and has a longer biological half-life than L-dopa. One can manipulate this ligand to form a chelate by means of either the α-amino acid functionality, or, by blocking the acid function by conversion to an ester, insure that the alkoxy phenol functionality will take precedence in chelate formation.

We claim:

1. A 1,2-disubstituted aromatic mineral chelate having the formula:

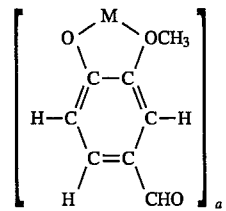

where a is an integer of 1 or 2 and M is a metal ion selected from the group consisting of Mg, Ca, Cr, Mn, Fe, Co, Cu, Zn, Mo and Se.

2. The chelate of claim 1 wherein M is Fe.
3. The chelate of claim 1 wherein M is Zn.
4. The chelate of claim 1 wherein M is Mn.
5. The chelate of claim 1 wherein M is Cu.
6. The chelate of claim 1 wherein M is Mg.
7. The chelate of claim 1 wherein M is Ca.
8. The chelate of claim 1 wherein M is Cr.
9. The chelate of claim 1 wherein M is Co.
10. The chelate of claim 1 wherein M is Mo.
11. The chelate of claim 1 wherein M is Se.
12. A method of promoting mineral uptake in a warm-blooded animal which comprises administering to said warm-blooded animal an effective amount of a 1,2-disubstituted aromatic mineral chelate having the formula:

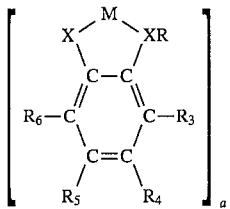

wherein a is an integer of 1, 2, or 3; M is a metal ion selected from the group consisting of Mg, Ca, Cr, Mn, Fe, Co, Cu, Zn, Mo, and Se; X is an electron donor member selected from the group consisting of O, S, or NH; R is a member selected from the group consisting of alkyl and alkenyl containing from 1 to 10 carbon atoms; $R_3$ and $R_6$ are independently members selected from the group consisting of H and R; $R_4$ and $R_5$ are independently members selected from the group consisting of H, R, R', $NH_2$, NHR, NHR', OH, SH, COOR, COOR', and CHO; and R' is an R group which had been additionally substituted by one or more members selected from the group consisting of COOH, $NH_2$, NHR, OH, SH, and COOR.

13. The method of claim 12 wherein a is 1 or 2.
14. The method of claim 13 wherein X is O.
15. The method of claim 14 wherein $R_3$, $R_5$ and $R_6$ are H.
16. The method of claim 15 wherein R is methyl.
17. The method of claim 16 wherein $R_4$ is H.
18. The method of claim 15 wherein $R_4$ is CHO.
19. The method of claim 18 wherein M is Fe.
20. The method of claim 18 wherein M is Zn.
21. The method of claim 18 wherein M is Mn.
22. The method of claim 18 wherein M is Cu.
23. The method of claim 18 wherein M is Mg.
24. The method of claim 18 wherein M is Ca.
25. The method of claim 18 wherein M is Cr.
26. The method of claim 18 wherein M is Co.
27. The method of claim 18 wherein M is Mo.
28. The method of claim 18 wherein M is Se.

* * * * *